(12) United States Patent
Wang et al.

(10) Patent No.: US 8,569,582 B2
(45) Date of Patent: Oct. 29, 2013

(54) METHOD FOR TRANSFORMATION OF GRASSES

(75) Inventors: Zeng-Yu Wang, Ardmore, OK (US); Rangaraj Nandakumar, Champaign, IL (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 447 days.

(21) Appl. No.: 12/820,426

(22) Filed: Jun. 22, 2010

(65) Prior Publication Data

US 2011/0030088 A1   Feb. 3, 2011

Related U.S. Application Data

(60) Provisional application No. 61/219,306, filed on Jun. 22, 2009.

(51) Int. Cl.
*C12N 15/84* (2006.01)
*A01H 4/00* (2006.01)

(52) U.S. Cl.
USPC ........... 800/294; 800/279; 800/284; 800/300; 800/302; 800/290; 800/285; 800/287; 800/275; 800/320

(58) Field of Classification Search
None
See application file for complete search history.

(56) References Cited

U.S. PATENT DOCUMENTS

| | | | |
|---|---|---|---|
| 5,563,055 A | 10/1996 | Townsend et al. | |
| 5,591,616 A | 1/1997 | Hiei et al. | |
| 7,611,898 B2 * | 11/2009 | Wang et al. | 435/469 |
| 7,862,829 B2 | 1/2011 | Johnston et al. | |
| 2003/0110531 A1 | 6/2003 | Dan et al. | |
| 2010/0235942 A1 | 9/2010 | Cai et al. | |

OTHER PUBLICATIONS

Ge et al. (Plant Cell Rep (2006) 25: 792-798).*
Wang and Ge (In Vitro Cell. Dev. Biol.—Plant 42:1-18, Jan.-Feb. 2006).*
Wang and Ge #2 (Journal of Plant Physiology, 162 (2005) 103-113).*
Cheng et al., "Invited review: factors influencing agrobacterium-mediated transformation of monocotyledonous species," In Vitro Cellular & Dev. Biol.—Plant, 40(1):37-45, 2004.
Fraley et al., "The SEV system: a new disarmed Ti plasmid vector system for plant transformation," Bio/technology, 3:629-635, 1985.
Hiei et al., "Transformation of rice mediated by Agrobacterium tumefaciens," Plant Mol. Biol., 35:205-218, 1997.
Ishida et al., "High efficiency transformation of maize (Zea mays L.) mediated by Agrobacterium tumefaciens," Nature Biotech., 14:745-750, 1996.
Janakiraman et al., "Recent advances in wheat transformation," In Vitro Cellular & Dev. Biol.—Plant, 38:404-414, 2002.
McCormac et al., "The use of visual marker genes as cell specific reporters of Agrobacterium-mediated T-DNA delivery to wheat," Euphytica, 99(1):17-25, 1998.
Rogers et al., "Improved vectors for plant transformation: expression cassette vectors and new selectable markers," Methods Enzymol., 153:253-277, 1987.
Somleva et al., "Agrobacterium-mediated genetic transformation of switchgrass," Crop Sci., 42:2080-2087, 2002.
Spangenberg et al., "Callus Cultures and Somaclonal Variation," In: Biotechnology in forage and turf grass improvement, Berlin, 1998.
Thomas et al., "Selection of interspecific somatic hybrids of medicago by using Agrobacterium-transformed tissues," Plant Sci., 69(2):189-198, 1990.
Tingay et al., "Agrobacterium tumefaciens-mediated barley transformation," Plant J., 11:1369-1376, 1997.
Wang et al., "Forage and turf grass biotechnology," Crit. Rev. Plant Sci., 20:573-619, 2001.

* cited by examiner

*Primary Examiner* — David T Fox
*Assistant Examiner* — Jared Shapiro
(74) *Attorney, Agent, or Firm* — Dentons US LLP (57) ABSTRACT

The invention provides methods for transforming grass plants with *Agrobacterium*. The invention allows creation of transgenic grass plants without the need for callus as a target tissue for transformation, thus providing a rapid method for the production of transgenic grass plants. Transgenic grass plants produced by this method are also provided.

13 Claims, 4 Drawing Sheets

METHOD FOR TRANSFORMATION OF GRASSES

This application claims priority to U.S. Provisional Application No. 61/219,306 filed on Jun. 22, 2009, which is incorporated herein by reference in its entirety.

BACKGROUND OF THE INVENTION

1. Field of the Invention

The present invention relates generally to the field of agricultural biotechnology. More specifically, the invention relates to transformation of grass plants using *Agrobacterium*-mediated gene transfer.

2. Description of the Related Art

Forage and grass plants are the backbone of sustainable agriculture and contribute extensively to the world economy. Switchgrass (*Panicum virgatum*), for instance, is a drought-resistant perennial C-4 warm-season grass native throughout North America and has recently been identified by the U.S. Department of Energy as a potential feedstock crop for the production of cellulosic biofuel. Among its beneficial characteristics for use as a cellulosic biomass source crop are high productivity, minimal nutrient needs, stand longevity, pest and disease resistance, water use efficiency, soil restoring properties, erosion control, wide geographic range, and adaptability to marginal soils. Other grass plants may also be of interest for production of lignocellulosic biomass. Genetic improvement of grass plants through biotechnological approaches could play a crucial role in modifying quantity or quality of biomass suitable for biofuel production. However, well defined, rapid and highly efficient genetic transformation systems for grass plants have thus far been lacking.

SUMMARY OF THE INVENTION

In one aspect, the invention provides a method of transforming a grass plant cell comprising contacting an explant from a grass plant with an *Agrobacterium* comprising a DNA of interest. In one embodiment, at least a first cell of the explant is transformed with the DNA of interest. In another embodiment, the explant is contacted with the *Agrobacterium* without first forming a callus culture of cells from the explant. The explant may also be excised from the plant prior to contacting the explant with the *Agrobacterium*. In particular embodiments, the grass plant is selected from the group consisting of: switchgrass, tall fescue, meadow fescue, perennial ryegrass, Italian ryegrass, orchardgrass, guinea grass, foxtail millet, pearl millet, bahiagrass and *Miscanthus*. In yet another embodiment, the explant is a nodal or inflorescence explant. In certain embodiments, the explant is a non-stolon or non-rhizome nodal explant.

In a further embodiment, the invention provides a transgenic grass plant produced by a method of the invention. In yet a further embodiment, methods are provided comprising culturing an explant after contacting the explant with *Agrobacterium* to induce formation of shoots or roots; allowing shoots or roots to form from the explant; and cultivating the explant under plant growth conditions to produce a transgenic grass plant comprising a DNA of interest. In still a further embodiment, the invention comprises growing a plant of the invention to sexual maturity and obtaining a transgenic seed therefrom.

In one embodiment, a DNA of interest is used according to the invention comprising a polynucleotide encoding a polypeptide, antisense construct or siRNA construct. In another embodiment, the polynucleotide is operably linked to a promoter functional in grass plants. The promoter may be a constitutive promoter, inducible promoter or tissue specific promoter. In yet another embodiment, the polynucleotide confers a trait selected from the group consisting of herbicide resistance, insect resistance, disease resistance, pest resistance, improved nutritional quality, modified carbohydrate metabolism, modified lipid metabolism, increased biomass, altered lignin content, increased plant digestibility, increased biomass digestibility, altered lignin biosynthesis, and modified fermentable carbohydrate content. In certain embodiments, the polypeptide comprises a selectable marker or a screenable marker. The selectable marker may confer resistance to a selective agent. In one embodiment, the invention provides contacting the explant with the selective agent and selecting an explant with tolerance to the agent.

In another aspect, the invention provides a $T_0$ nodal or inflorescence explant generated in accordance with methods of the invention. In yet another aspect, the invention provides a cell of the explant of the present invention.

In a further aspect, the invention provides a method of producing food, feed or biomass, comprising (a) obtaining a plant in accordance with the methods of the present invention; and (b) producing food, feed or biomass from the plant or part thereof.

In yet a further aspect, the invention provides a method of plant breeding comprising (a) obtaining a plant in accordance with the methods of the present invention; and (b) crossing said plant with a second grass plant.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

DETAILED DESCRIPTION OF THE INVENTION

The invention provides methods for genetic transformation of grass plants. In one embodiment the grass plant may be switchgrass, tall fescue, meadow fescue, perennial ryegrass, Italian ryegrass, orchardgrass, guinea grass, foxtail millet, pearl millet, bahiagrass or *Miscanthus*. In another embodiment, the grass plant is a non-stoloniferous plant or a plant that does not form stolons or rhizomes.

Compared to previous methods, the procedures described allow direct transformation from explants without requiring callus production and thus significantly reducing the time required to produce transgenic plants. The bypass of callus explants also decreases labor and complications associated with tissue culture, while surprisingly allowing an even higher transformation efficiency.

Initial methods for transforming monocot plants involved direct gene transfer to protoplasts, then by biolistic transformation, and in more recent years by *Agrobacterium*-mediated transformation (Cheng et al., 2004; Janakiraman et al., 2002; Spangenberg et al., 1998; Wang et al., 2001). Previous methods for producing transgenic grass plants, such as switchgrass involved use of embryogenic calli, which is time consuming, often taking greater than six months to obtain a transformed plant. Additionally, callus induction and plant regeneration from the induced callus can cause somaclonal variation (Choi et al., 2000; Goldman et al., 2004; Spangenberg et al., 1998). When callus is used for transformation, the final transformation efficiency depends upon the frequency of embryogenic callus formation, the percentage of resistant calluses obtained after antibiotic selection, as well as the frequency of plant regeneration from the resistant calluses. Methods for direct transformation provided herein, however, are rapid and efficient. There is also no need for laborious maintenance of callus cultures and cell lines. The providing of a method allowing callus-free rapid transformation of grass plants represents a significant advance.

Like many forage and turf grasses, switchgrass is outcrossing and highly heterozygous, individual seeds/embryos from the same cultivar may represent different genotypes. When calluses are induced from different seeds/embryos, it would be impossible to exclude genotypic effects in the regenerants or transformants (Wang et al., 2003; Wang et al., 2004). The use of explants, for instance from nodes or inflorescences, for direct transformation can allow for the generation of transformants from selected genotypes, thus permitting genotypic effects to be excluded in the regenerants and allowing for direct comparison and evaluation of transgene effects in a given selected uniform background.

Improvement of forage and turf grasses by conventional breeding is slow due to the genetic complexity of these species (Ha et al., 1992; Spangenberg et al., 1998). However, they can be excellent targets for biotechnological improvement because of the unique characteristics of many of these species.

Switchgrass has recently been identified by the U.S. Department of Energy as a potential herbaceous feedstock crop for the production of cellulosic biofuel. Because of its high productivity, low nutrient and water requirements, adaptation to marginal soils, flexibility for multipurpose uses, low cost of production and environmental benefits, switchgrass has been developed into a model herbaceous biofuel crop (Keshwani and Cheng, 2009; McLaughlin and Walsh, 1998; McLaughlin and Kszos, 2005). Other grass plants may also be useful sources for biofuels. However, lignin in the biomass of these grass plants may interfere with the availability of cellulose and hemicellulose as sources of fermentable sugar. Consequently, genetic manipulation of the biomass source grass plant, such as switchgrass, can play a crucial role in modifying quantity or quality of biomass suitable for biofuel production.

The potential for genetic manipulation of lignin content and composition to improve the digestibility of forage crops has been studied (Dixon, et al., 1994; Tabe, et al., 1993; Whetten and Sederoff, 1991; U.S. Patent Appl. Pub. 2004/0049802.). Small decreases in lignin content have been reported to positively impact the digestibility of forages (Casler, 1987). With respect to ethanol production, genetic modification to reduce or alter the lignin content of dedicated biomass crops might significantly improve the efficiency of cellulose hydrolysis, increasing the yield of fermentable sugars from the biomass (e.g. Sticklen, 2006). However, many grass plants, for instance, switchgrass, are considered recalcitrant to genetic transformation (Wang and Ge, 2006). The present invention overcomes deficiencies in the art by providing a rapid and highly efficient method of transforming, and thus genetically modifying grass plants, for instance switchgrass, tall fescue, meadow fescue, perennial ryegrass, Italian ryegrass, orchardgrass, guinea grass, foxtail millet, pearl millet, bahiagrass and *Miscanthus*. In one embodiment, this method will be useful in producing grass plants as a source for biofuels.

Further, with the availability of more and more EST (expressed sequence tag) sequence information in grasses, as well as simplified molecular cloning techniques, gene isolation has become easier than ever before, the test of gene functions in transgenic plants has become the bottleneck. Thus, the development of an efficient *Agrobacterium*-mediated transformation system for grasses opens up new opportunities for functional characterization of genes and promoters.

While direct gene transfer to protoplasts remains useful for transient expression assays, biolistic and *Agrobacterium*-mediated transformation are the two major methods for generating transgenic plants in monocots (Cheng et al., 2004; Janakiraman et al., 2002; Wang et al., 2001). *Agrobacterium*-mediated transformation has received more attention in recent years, because it has the advantage of allowing for the stable integration of a defined DNA segment into the plant genome and generally results in a lower copy number, fewer rearrangements and an improved stability of expression over generations than the free DNA delivery methods (Dai et al., 2001; Hu et al., 2003).

Callus culture has been an inevitable step in monocot and other plant transformation protocols and in particular, switchgrass transformation. In many transformation protocols, calluses were used as direct target for microprojectile bombardment or for *Agrobacterium* infection (Cheng et al., 2003; Cho et al., 2001; Hartman et al., 1994; Li and Qu, 2004; Sallaud et al., 2003; Spangenberg et al., 1998; Spangenberg et al., 1995; Vasil et al., 1992; Wan and Lemaux, 1994; Wang et al., 2004; Wang and Ge, 2005). In other protocols, freshly isolated immature embryos or shortly pre-cultured embryos were used as target for microprojectile bombardment or for *Agrobacterium* infection (Aldemita and Hodges, 1996; Frame et al., 2002; Hu et al., 2003; Huber et al., 2002; Popelka and Altpeter, 2003; Tingay et al., 1997; Wan and Lemaux, 1994; Zhao et al., 2000), and calluses were later induced from the bombarded or infected embryos.

The present invention thus provides a rapid and efficient transformation protocol based on direct explant *Agrobacte-*

*rium*-mediated transformation of grass plants. The protocol has been successfully tested in both nodal and inflorescence switchgrass explants. Rapid production of transgenic plant lines was achieved with a transformation efficiency of 4%. These results described in detail in the Examples below demonstrate a significant improvement for genetic transformation of switchgrass plants. However, the methods of the present invention may also be applied advantageously to other grasses such as, tall fescue, meadow fescue perennial ryegrass, Italian ryegrass, orchardgrass, guinea grass, foxtail millet, pearl millet, bahiagrass and *Miscanthus*.

In one embodiment, the methods of the invention may be applied to non-stoloniferous plants or plants that do not form stolons or rhizomes. In another embodiment, the explant is a non-stolon or non-rhizome node or a node from a shoot that does not produce adventitious roots.

I. AGROBACTERIUM

A. Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells generally is well known in the art. See, for example, the methods described by Fraley et al. (1985), Rogers et al. (1987) and U.S. Pat. No. 5,563,055, specifically incorporated herein by reference in its entirety. Of particular interest in transformation protocols is *A. tumefaciens*.

It is understood that by *Agrobacterium*, applicants include *Rhizobium* species known to act in the same manner as, for example, *A. tumefaciens* for purposes of plant transformation. Such species include *Rhizobium* spp., including *Rhizobium leguminosarum* and the like.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. Vectors known in the art may have convenient multi-linker regions flanked by a promoter and a polyadenylation site for direct expression of inserted polypeptide coding genes and are suitable for present purposes (Rogers et al., 1987). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

The following patents relate to *Agrobacterium* transformation methods and are hereby incorporated by reference: U.S. Pat. Nos. 6,846,971, 6,822,144, 6,800,791, 6,759,573, 6,696, 622. 6,686,515, 6,664,108, 6,620,986, 6,603,061, 6,455,761, 6,420,630, 6,384,301, 6,369,298, 6,323,396, 6,307,127, 6,300,545, 6,274,791, 6,265,638, 6,255,559, 6,255,115, 6,215,051, 6,162,965, 6,103,955, 6,074,877, 6,074,876, 6,051,757, 6,040,498, 6,037,522, 5,994,624, 5,981,840, 5,977,439, 5,952,543, 5,948,956, 5,932,782, 5,929,300, 5,922,928, 5,919,919, 5,846,797, 5,824,877, 5,824,872, 5,750,871, 5,733,744, 5,712,112, 5,693,512, 5,689,053, 5,591,616, 5,589,615, 5,569,834, 5,565,347, 5,563,055, 5,530,182, 5,463,174, 5,416,011, 5,262,316, 5,188,958, 5,159,135, 5,004,863, 4,954,442, and 4,795,855.

II. TRANSFORMATION CONSTRUCTS, NUCLEIC ACIDS AND POLYPEPTIDES

Various coding sequences may be provided operably linked to a heterologous promoter, in either sense or antisense orientation and used to transform grass plants according to the present invention. *Agrobacterium* expression constructs (above) are provided comprising such sequences, as are plants and plant cells transformed with the sequences. The construction of *Agrobacterium* vectors which may be employed in conjunction with plant transformation techniques using these or other sequences according to the invention will be known to those of skill of the art in light of the present disclosure. The techniques of the current invention are thus not limited to any particular nucleic acid sequences, and the following merely provide examples of genes suitable for transfer and expression into plants.

A. Coding Sequences i. Lignin Biosynthesis

One example of a beneficial modification that may be made to plants is to lignin content. Lignin is a major structural component of secondarily thickened plant cell walls. It is a complex polymer of hydroxylated and methoxylated phenylpropane units, linked via oxidative coupling (Boudet et al., 1995). Because of the negative effects of lignin on forage quality, there is considerable interest in genetic manipulation to alter the quantity and/or quality of the lignin polymer (Dixon et al., 1996). At the same time, lignin is important for stem rigidity and hydrophobicity of vascular elements, and, particularly in cereal crops, may be an important inducible defensive barrier against fungal pathogen attack (Beardmore et al., 1983). Thus, lignin modification must not compromise basic functions for the plant and thereby result in negative traits such as lodging or disease susceptibility.

Examples of genes that may be modified include enzymes of the monolignol pathway, such as caffeic acid 3-O-methyltransferase (COMT), caffeoyl CoA 3-O-methyltransferase (CCoAOMT) and cinnamyl alcohol dehydrogenase (CAD). Constitutive cauliflower mosaic virus 35S promoter-driven antisense reduction of COMT to less than 5% of wild-type values in the tropical pasture legume *Stylosanthes humilis* resulted in a strong reduction in S lignin based on histochemical analysis, for example (Rae et al., 2001). In vitro digestibility of stem material in rumen fluid was increased by up to 10% in the transgenic plants exhibiting strongest COMT down-regulation.

Other lignin biosynthesis genes that may be modified include the following: 4-coumarate 3-hydroxylase (C3H), phenylalanine ammonia-lyase (PAL), cinnamate 4-hydroxylase (C4H), hydroxycinnamoyl transferase (HCT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH).

ii. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al. (1988); Gleen et al. (1992) and Miki et al. (1990).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835, which discloses the nucleotide sequence of a form of EPSPS which can confer glyphosate resistance. Examples of specific EPSPS transformation events conferring glyphosate resistance are provided by U.S. Pat. No. 6,040,497.

A DNA molecule encoding a mutant aroA gene can be obtained under ATCC accession number 39256, and the nucleotide sequence of the mutant gene is disclosed in U.S. Pat. No. 4,769,061 to Comai. EPA No. 0 333 033 and U.S. Pat. No. 4,975,374 disclose nucleotide sequences of glutamine synthetase genes which confer resistance to herbicides such as L-phosphinothricin. The nucleotide sequence of a phosphinothricin-acetyltransferase gene is provided in EPA No. 0 242 246. DeGreef et al. (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acct-S1, Accl-S2 and Acct-S3 genes described by Marshall et al. (1992).

Genes are also known conferring resistance to a herbicide that inhibits photosynthesis, such as a triazine (psbA and gs+genes) and a benzonitrile (nitrilase gene). Przibila et al. (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (1992).

iii. Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al. (1994) (cloning of the tomato Cf-9 gene for resistance to *Cladosporium fulvum*); Martin et al. (1993) (tomato Pto gene for resistance to *Pseudomonas syringae* pv.); and Mindrinos et al. (1994) (*Arabidopsis* RSP2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al. (1993), who show that transgenic plants expressing recombinant antibody genes are protected from virus attack. Logemann et al. (1992), for example, disclose transgenic plants expressing a barley ribosome-inactivating gene have an increased resistance to fungal disease.

iv. Insect Resistance

One example of an insect resistance gene includes a *Bacillus thuringiensis* protein, a derivative thereof or a synthetic polypeptide modeled thereon. See, for example, Geiser et al.

(1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al. (1994), who disclose the nucleotide sequences of several *Clivia miniata* mannose-binding lectin genes. A vitamin-binding protein may also be used, such as avidin. See PCT application WO 94/000992, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al. (1987) (nucleotide sequence of rice cysteine proteinase inhibitor), Huub et al. (1993) (nucleotide sequence of cDNA encoding tobacco proteinase inhibitor I), and Sumitani et al. (1993) (nucleotide sequence of *Streptomyces nitrosporeus* α-amylase inhibitor). An insect-specific hormone or pheromone may also be used. See, for example, the disclosure by Hammock et al. (1990), of baculovirus expression of cloned juvenile hormone esterase, an inactivator of juvenile hormone.

Still other examples include an insect-specific antibody or an immunotoxin derived therefrom and a developmental-arrestive protein. See Taylor et al. (1994), who described enzymatic inactivation in transgenic tobacco via production of single-chain antibody fragments.

v. Modified Fatty Acid, Phytate and Carbohydrate Metabolism

Genes may be used conferring modified fatty acid metabolism. For example, stearyl-ACP desaturase genes may be used. See Knutzon et al. (1992). Various fatty acid desaturases have also been described, such as a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al., 1992); a gene encoding a stearoyl-acyl carrier protein delta-9 desaturase from castor (Fox et al., 1993); Δ6- and Δ12-desaturases from the cyanobacteria *Synechocystis* responsible for the conversion of linoleic acid (18:2) to gamma-linolenic acid (18:3 gamma) (Reddy et al., 1993); a gene from *Arabidopsis thaliana* that encodes an omega-3 desaturase (Arondel et al., 1992); plant Δ9-desaturases (PCT Application Publ. No. WO 91/13972) and soybean and *Brassica* Δ15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al. (1993), for a disclosure of the nucleotide sequence of an *Aspergillus niger* phytase gene. In corn, this, for example, could be accomplished by cloning and then reintroducing DNA associated with the single allele which is responsible for corn mutants characterized by low levels of phytic acid. See Raboy et al. (2000).

A number of genes are known that may be used to alter carbohydrate metabolism. For example, plants may be transformed with a gene coding for an enzyme that alters the branching pattern of starch. See Shiroza et al. (1988) (nucleotide sequence of *Streptococcus mutants* fructosyltransferase gene), Steinmetz et al. (1985) (nucleotide sequence of *Bacillus subtilis* levansucrase gene), Pen et al. (1992) (production of transgenic plants that express *Bacillus lichenifonnis* α-amylase), Elliot et al. (1993) (nucleotide sequences of tomato invertase genes), Sergaard et al. (1993) (site-directed mutagenesis of barley α-amylase gene), and Fisher et al. (1993) (maize endosperm starch branching enzyme II). The Z10 gene encoding a 10 kD zein storage protein from maize may also be used to alter the quantities of 10 kD Zein in the cells relative to other components (Kirihara et al., 1988).

B. Antisense and RNAi Constructs

In the methods and compositions of the present invention, lignin biosynthesis can be altered or the activity of genes or proteins of interest can be down-regulated by any means known in the art, including through the use of ribozymes, aptamers, antisense, RNAi miRNA, trans-acting siRNA and the like. In particular, constructs comprising any gene of interest, including fragments thereof, in antisense orientation, or combinations of sense and antisense orientation, may be used to decrease or effectively eliminate the expression of the desired gene in a plant. Accordingly, this may be used to "knock-out" the function of a gene of interest.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 21, 30, 50, 75 or 100 or more contiguous nucleic acids of the nucleic acid sequence of any gene of interest, and/or complements thereof, which may be in sense and/or antisense orientation. By including sequences in both sense and antisense orientation, increased suppression of the corresponding coding sequence may be achieved.

Constructs may be designed that are complementary to all or part of the gene of interest or promoter and other control regions, exons, introns or even exon-intron boundaries of a gene. It is contemplated that the most effective constructs may include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. Methods for selection and design of sequences that generate RNAi are well known in the art (e.g. Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

C. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Llewellyn et al., 1987), sucrose synthase (Yang and Russell, 1990), α-tubulin, actin (Wang et al., 1992), cab (Sullivan et al., 1989), PEPCase (Hudspeth and Grula, 1989) or those promoters associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of an acid phosphatase coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots.

D. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of an acid phosphatase coding sequence is used. Alternatively, a heterologous 3' end may enhance the expression of sense or antisense acid phosphatase coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

E. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

F. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. SELECTION, PRODUCTION AND CHARACTERIZATION OF STABLY TRANSFORMED GRASS PLANTS

After effecting delivery of exogenous DNA to recipient grass plant cells, steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population for example, a node or inflorescence, by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973).

Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987), *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 weeks to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 weeks on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a gene. Both PCR and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting, in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. BREEDING PLANTS OF THE INVENTION

In addition to direct transformation of a particular grass plant genotype with a construct according to the current invention, transgenic grass plants may be made in crosses with a transformed grass plant having a selected DNA and a second grass plant. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:
  (a) plant seeds of the first (starting line) and second (donor plant line that comprises a transgene) parent plants;
  (b) grow the seeds of the first and second parent plants into plants that bear flowers;
  (c) pollinate a flower from the first parent plant with pollen from the second parent plant; and
  (d) harvest seeds produced on the parent plant bearing the fertilized flower.

Backcrossing is herein defined as the process including the steps of:
  (a) crossing a plant of a first genotype containing a desired gene, DNA sequence or element to a plant of a second genotype lacking the desired gene, DNA sequence or element;
  (b) selecting one or more progeny plant containing the desired gene, DNA sequence or element;
  (c) crossing the progeny plant to a plant of the second genotype; and
  (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly, a plant genotype lacking the desired DNA sequence may be referred to as an unconverted genotype, line, inbred, or hybrid.

V. DEFINITIONS

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Inflorescence: A group or cluster of flowers arranged on one or a series of branches on a plant stem.

Node: The point on a plant stem where a leaf is or has been attached. In one embodiment, nodes from non-stolon or non-rhizome shoots are used as explants in methods according to the invention.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA that has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VI. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Plant Material, Bacterial Strains and Binary Vector

Two switchgrass genotypes ST-1 and ST-2, derived from the lowland cultivar Alamo were used for explants collection. For nodal explants, top two nodes at E3 or E4 stage were collected from the greenhouse grown plants and cut into 3 cm pieces 1.5 cm above and below the node. The nodal segments were surface sterilized with 70% ethanol for 2 minutes, followed by 20% bleach for 15 minutes and then rinsed three times with sterile water. About 0.5 cm above and below node segments were again cut, split longitudinally and used for bacterial infection.

For inflorescences explants, top nodes about 10 cm at E4 stage were cut, surface sterilized with 70% ethanol for 10 minutes and pre-cultured on MSB medium (MS basal salts, 3 mg/l BAP) for 10 days. The pre-cultured inflorescences were cut into small pieces, transferred onto SM5 medium (MS basal salts, 5 mg/l 2,4-D) and cultured for 10 days before infection. Alternatively, the pre-cultured inflorescences were cut into small pieces and directly used for *Agrobacterium* infection. All tissue culture media in this study contained MS salts, 3% sucrose and 7.5 g/l agar. *Agrobacterium tumefaciens* strain, EHA105 harboring pCAMBIA1305.1 (CAMBIA, Canberra) carrying the 35SCaMV promoter driving the hygromycin-resistant gene (hpt) and the β-glucuronidase gene (gus) was used.

Example 2

Transformation of Switchgrass Explants

The *Agrobacterium* strain EHA105 containing pCMABIA1305.1 vector was used for direct transformation of nodes and inflorescences of switchgrass. *Agrobacteria* were grown in 50 ml LB liquid medium containing respective antibiotics on a rotary shaker at 200 rpm for 24 hours at 28° C. Two to three hours before the harvest of bacterial cells, 200 µM acetosyringone was added to induce the virulence genes. Bacterial cells were harvested by centrifugation at 4000 rpm for 15 minutes and resuspended in inoculation medium (MS salts with 20 mM MES, 2 mg/l BAP, pH 5.6). The density of the bacterial solutions was adjusted to 1.0 ($OD_{600}$) by using inoculation medium. The nodal explants or pre-cultured inflorescences were immersed in culture vessels and vacuum infiltrated for 30 minutes. After the vacuum valve was released, the explants were incubated with Agrobacterial solution for another 30 minutes. Inoculated nodes or inflorescences were then blot dried on sterile filter paper and cocultivated on filter paper wetted with 1 ml of inoculation medium containing 200 µM acetosyringone. After three days of cocultivation in the dark at 24° C., nodes were washed with sterile distilled water containing 500 mg/l cefotaxime and cultured for 7-10 days on MSB or SM5 resting medium with 500 mg/l cefotaxime.

Example 3

Selection and Regeneration of Transformed Explants

Simultaneous selection and shoot regeneration or callus induction was followed for nodes and inflorescences. Three cocultivation experiments were performed for nodes and four experiments for inflorescences. After resting, nodal segments were transferred onto MSB medium containing 30 mg/l hygromycin, 250 mg/l cefotaxime and cultured for 3-4 weeks. Dead and long shoots were trimmed off and shoots were transferred onto MSB medium with 50 mg/l hygromycin and cultured for 30 days. Developed new shoots were transferred into MSO rooting medium (half-strength of MSB medium, 2 mg/l BAP).

Figure 1:
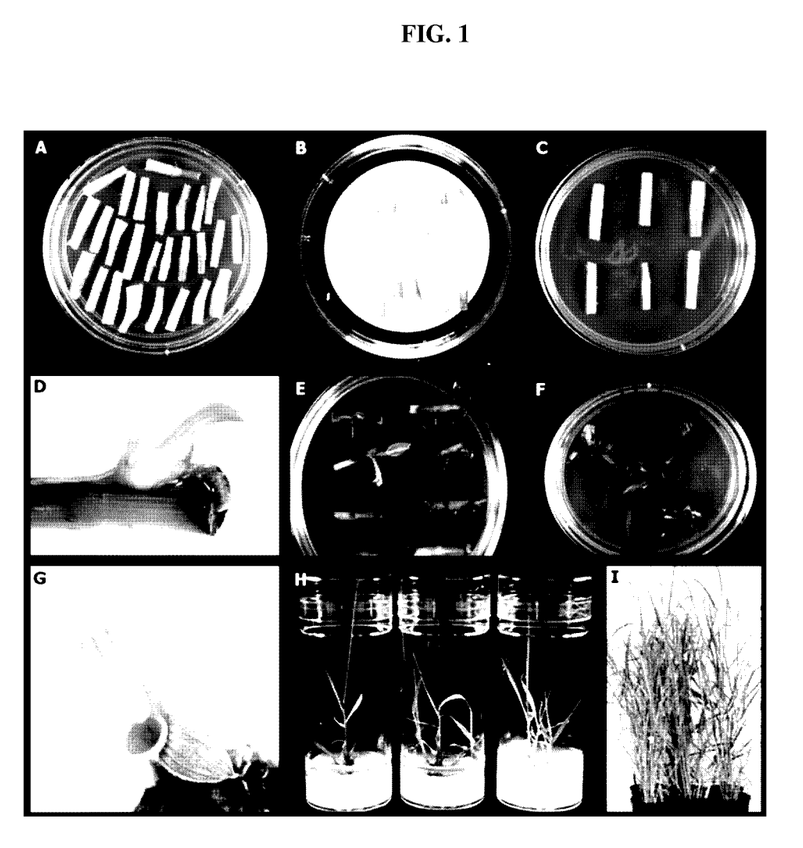
FIG. 1. Direct transformation of switchgrass using nodal explants. (A) and (B) Cocultivation of nodes on MSB medium or filter paper supplemented with 200 μm acetosyringone. (C) Resting of infected nodes on MSB medium. (D) Shoot initiation from split node after resting period. (E) Green shoot produced 30 days after hygromycin selection. (F) and (G) New green shoots produced 60 days after hygromycin selection. (H) Rooted transgenic plants obtained 12 weeks after transformation. (I) Greenhouse grown transgenic plants.

Nodes from different switchgrass genotypes were used for infection (FIG. 1). After infection, 50% of the nodes produced shoots on MSB medium with low level of hygromycin (30 mg/l) selection. Although most of the initially formed nodes were killed during the second selection (50 mg/l hygromycin), the new shoots formed during this period were hygromycin resistant shoots and the frequency of resistant shoots formed during high level hygromycin selection was around 10%. A total of 16 putative hygromycin resistant lines were produced from node transformation.

Figure 2:
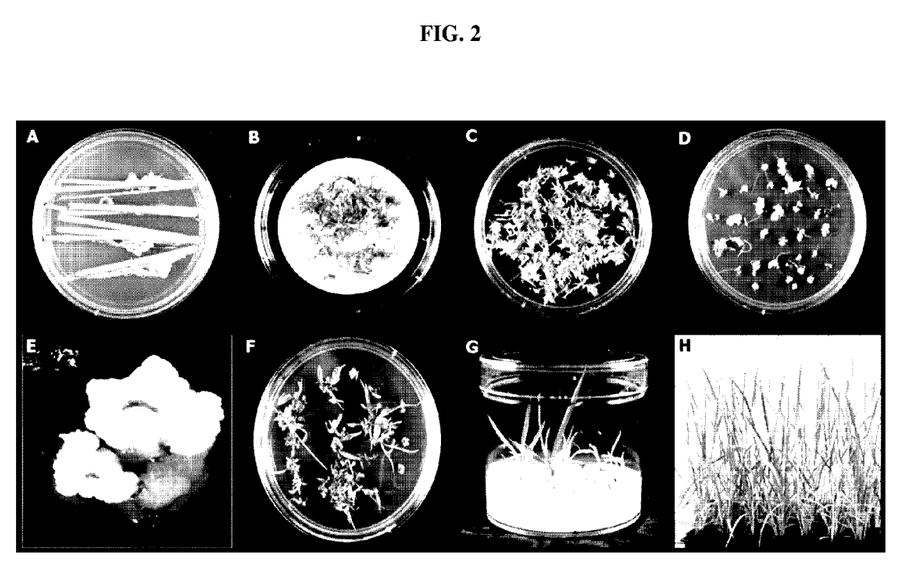
FIG. 2. Direct transformation of switchgrass using inflorescences explants. (A) Pre-culturing of inflorescences on MSB medium. (B) and (C) Cocultivation of pre-cultured inflorescences on SM5 medium or filter paper supplemented with 200 μm acetosyringone. (D) and (E) Hygromycin resistant calli produced 30 days after hygromycin selection. (F) Regenerated hygromycin resistant calli on MSK medium. (G) Rooted transgenic plants obtained 12 weeks after transformation (compared with non transgenic plants on hygromycin containing medium). (H) Greenhouse grown transgenic plants.

Inflorescences pre-cultured on MSB or SM5 medium were used for *Agrobacteria* infection (FIG. 2). Two types of selection procedures were followed. For a first set of experiments, infected inflorescences were selected on SM5 medium containing 40 mg/l hygromycin for 5 weeks. For another set of experiments, the surviving resistant calli after first selection, were subcultured onto SM5 medium supplemented with 50 mg/l hygromycin. Resistant calli were regenerated on MS medium with 0.2 mg/l kinetin, 0.15 mg/l BAP. Well developed shoots were then rooted on hormone-free half strength MSO rooting medium. Plantlets with well developed roots were transferred to soil and grown under greenhouse conditions.

Most of the MSB pre-cultured inflorescence died on selection medium and did not produce calli. Pre-culturing on both MSB and SM5 medium helped to produce hygromycin resistant calli after selection. A total 20 transgenic plants were generated after 2 months of selection.

Example 4

PCR and RT-PCR Analysis for hpt and gus Genes

Polymerase chain reactions were carried out on genomic DNA and RNA from transgenic and non-transgenic plants using primers specific for hpt, gus, efl (elongation factor) and Atu0792 (*Agrobacterium* chromosomal gene). Total DNA and RNA were isolated using CTAB and TRI reagent, respectively. Reverse transcriptase reactions were carried using Qiagen ominiscript RT Kit. PCR reactions were performed using Promega GoTaq® Master Mix Kit, in a 25 µl reaction mixture containing 1 µl of total DNA (200 ng) or cDNA, 12.5 µl of green GoTaq® 2X PCR buffer (DNA Polymerase, 0.1 unit/µl, 3 mM $MgCl_2$, 400 µM each dNTP), 1 µl of each primer (5 pmol of each forward and reverse) and 9.5 µl of sterile distilled water. The hpt, gus, efl and Atu0792 sequences were amplified with the following temperature conditions: Pre incubation at 95° C. for 2 minutes, followed by 33 cycles of denaturation at 94° C. for 30 seconds, annealing at 55° C. for 30 seconds and synthesis at 72° C. for 30 seconds, followed by a final extension at 72° C. for 10 minutes. The amplified PCR product (10 µl) was subjected to electrophoresis on a 1% agarose gel and visualized under UV light. The expected sizes of PCR products were 398, 472, 500 and 500 bp for hpt, gus, efl and Atu0792 genes, respectively.

Figure 3:
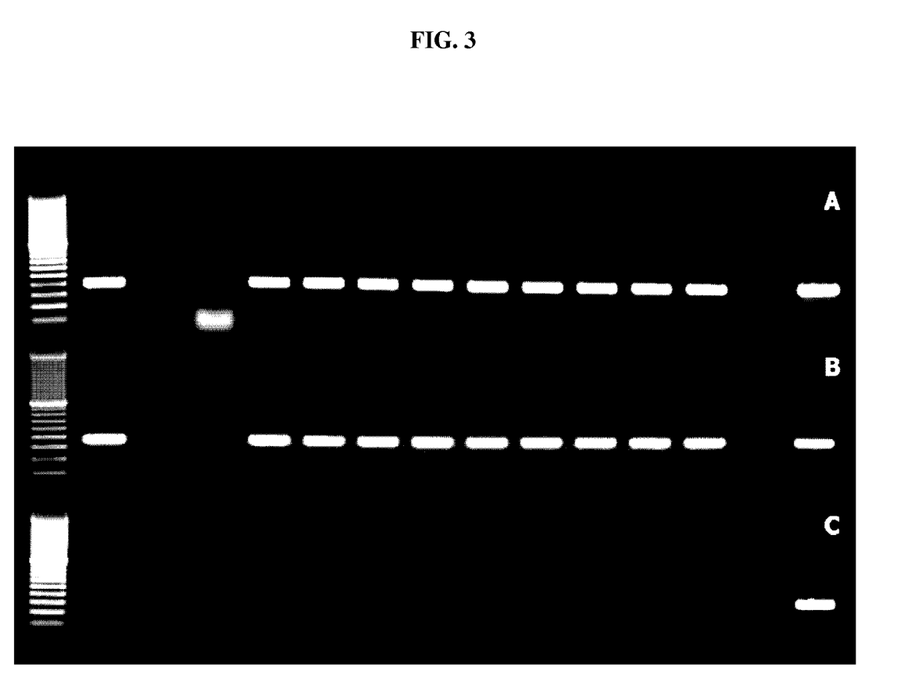
FIG. 3. PCR analysis for (A) hpt, (B) gus and (C) Atu0792 genes in greenhouse grown transgenic plants obtained from node transformation. Lane designations are as follows: M: 100 bp marker; PC: Positive control; WC: water control; NC: nontransformed control; 1-9: transgenic plants; and 10: *Agrobacterium* EHA105 strain.
Figure 4:
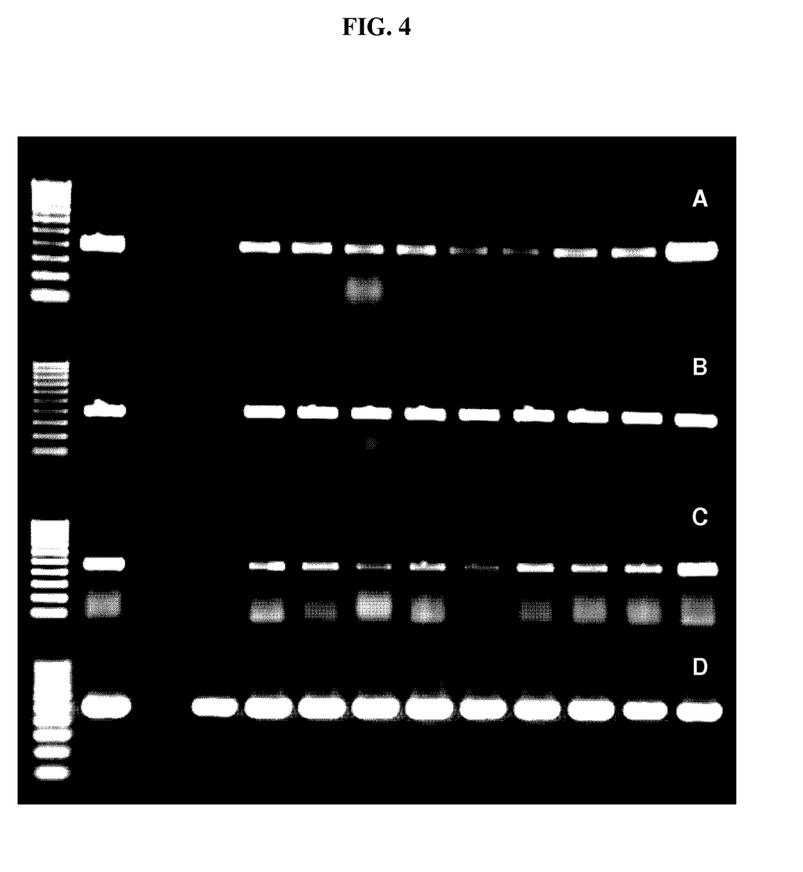
FIG. 4. RT-PCR analysis of RNA isolated from greenhouse grown transgenic plants obtained from node transformation. (A) hpt (29 cycles); (B) hpt (32 cycles); (C) gus (32 cycles); (D) efl (29 cycles). Lane designations are as follows: M: 100 by marker; PC: positive control; WC: water control; NC: nontransformed control; and 1-9: transgenic plants.

PCR analysis of node transgenic lines indicated that seven lines were positive for both hpt and gus genes. Bands of the expected size of 398 and 472 bp were obtained for hpt and gus genes, respectively (FIG. 3). Results were confirmed by repeating the PCR analysis in three independent experiments. It was also confirmed that the amplification of PCR products was not due to Agrobacterial contamination. RT-PCR analysis demonstrated the expression of hpt and gus genes in transgenic lines (FIG. 4).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060; U.S. Pat. No. 4,769,061; U.S. Pat. No. 4,795,855; U.S. Pat. No. 4,810,648; U.S. Pat. No. 4,940,835; U.S. Pat. No. 4,954,442; U.S. Pat. No. 4,975,374; U.S. Pat. No. 5,004,863; U.S. Pat. No. 5,159,135; U.S. Pat. No. 5,188,958; U.S. Pat. No. 5,262,316; U.S. Pat. No. 5,416,011; U.S. Pat. No. 5,463,174; U.S. Pat. No. 5,530,182; U.S. Pat. No. 5,545,818; U.S. Pat. No. 5,550,318; U.S. Pat. No. 5,563,055; U.S. Pat. No. 5,563,055; U.S. Pat. No. 5,565,347; U.S. Pat. No. 5,569,834; U.S. Pat. No. 5,589,615; U.S. Pat. No. 5,591,616; U.S. Pat. No. 5,689,053; U.S. Pat. No. 5,693,512; U.S. Pat. No. 5,712,112; U.S. Pat. No. 5,733,744; U.S. Pat. No. 5,750,871; U.S. Pat. No. 5,824,872; U.S. Pat. No. 5,824,877; U.S. Pat. No. 5,846,797; U.S. Pat. No. 5,919,919; U.S. Pat. No. 5,922,928; U.S. Pat. No. 5,929,300; U.S. Pat. No. 5,932,782; U.S. Pat. No. 5,948,956; U.S. Pat. No. 5,952,543; U.S. Pat. No. 5,977,439; U.S. Pat. No. 5,981,840; U.S. Pat. No. 5,994,624; U.S. Pat. No. 6,037,522; U.S. Pat. No. 6,040,497; U.S. Pat. No. 6,040,498; U.S. Pat. No. 6,051,757; U.S. Pat. No. 6,074,876; U.S. Pat. No. 6,074,877; U.S. Pat. No. 6,103,955; U.S. Pat. No. 6,162,965; U.S. Pat. No. 6,215,051; U.S. Pat. No. 6,255,115; U.S. Pat. No. 6,255,559; U.S. Pat. No. 6,265,638; U.S. Pat. No. 6,274,791; U.S. Pat. No. 6,300,545; U.S. Pat. No. 6,307,127; U.S. Pat. No. 6,323,396; U.S. Pat. No. 6,369,298; U.S. Pat. No. 6,384,301; U.S. Pat. No. 6,420,630; U.S. Pat. No. 6,455,761; U.S. Pat. No. 6,603,061; U.S. Pat. No. 6,620,986; U.S. Pat. No. 6,664,108; U.S. Pat. No. 6,686,515; U.S. Pat. No. 6,696,622; U.S. Pat. No. 6,759,573; U.S. Pat. No. 6,800,791; U.S. Pat. No. 6,822,144; U.S. Pat. No. 6,846,971

U.S. Patent Appl. Pub. 2004/0049802
Abe et al., *J. Biol. Chem.*, 262:16793, 1987.
Aldemita and Hodges, *Planta*, 199:612-617, 1996.
Arondel et al., *Science*, 258(5086):1353-1355 1992.
Beachy et al., *Ann. Rev. Phytopathol.*, 28:451, 1990.
Bevan et al., *Nucleic Acids Res.*, 11(2):369-385, 1983.
Casler, M. D., *Crop Sci* 27:931-934, 1987.
Callis et al., *Genes Dev.*, 1:1183-1200, 1987.
Chandler et al., *Plant Cell*, 1:1175-1183, 1989.
Chen et al., *Plant Biotechnol. J.*, 1:437-449, 2003.
Cheng et al., *In Vitro Cell. Dev. Biol.-Plant*, 39, 595-604, 2003.
Cheng et al., *In Vitro Cell. Dev. Biol.-Plant*, 40, 31-45, 2004.
Cho et al., *Plant Cell Rep.*, 20:318-324, 2001.
Choi et al., *Crop Sci.*, 40:524-533, 2000.
Chu et al., *Scientia Sinica*, 18:659-668, 1975.
Conkling et al., *Plant Physiol.*, 93:1203-1211, 1990.
Dai et al., *Mol. Breed.*, 7:25-33, 2001.
DE Appln. 3642 829
De Block et al., *EMBO J.*, 6(9):2513-2518, 1987.
De Block et al., *Plant Physiol.*, 91:694-701, 1989.
Dellaporta et al., In: *Chromosome Structure and Function: Impact of New Concepts*, 18th Stadler Genetics Symposium, 11:263-282, 1988.
Downward, *B M J*, 328(7450):1245-1248, 2004.
Ebert et al., *Proc. Natl. Acad. Sci. USA*, 84:5745-5749, 1987.
Elliot et al., *Plant Molec. Biol.*, 21:515, 1993.
European Appln. 0 242 246
European Appln. 0 333 033
European Appln. 0616644
European Appln. 154 204
Fisher et al., *Plant Physiol.*, 102:1045, 1993.
Fire et al., *Nature*, 391: 806-11, 1998.
Fox et al. *Proc. Natl. Acad. Sci. USA*, 90(6):2486-2490, 1993.
Fraley et al., *Bio/Technology*, 3:629-635, 1985.
Frame et al., *Plant Physiol.*, 129:13-22, 2002.
Fromm et al., *Nature*, 319(6056):791-793, 1986.
Gallie et al., *The Plant Cell*, 1:301-311, 1989.
Geiser et al., *Gene*, 48:109, 1986.
Gleen et al., *Plant Molec. Biology*, 18:1185-1187, 1992.
Goldman et al., *Plant Cell Rep.*, 22:553-560, 2004.
Ha et al., *Plant Cell Rep.*, 11:601-604, 1992.
Hammock et al., *Nature*, 344:458, 1990.
Hartman et al., *Bio/Technology*, 12:919-923, 1994.
Haseloff et al., *Proc. Natl. Acad. Sci. USA*, 94(6):2122-2127, 1997.
Hayes et al., *Biochem. J.*, 285(Pt 1):173-180, 1992.
Hiei et al., *Plant Mol. Biol.*, 35(1-2):205-218, 1997.
Hinchee et al., *Bio/technol.*, 6:915-922, 1988.
Hu et al., *Plant Cell Rep.*, 21:1010-1019, 2003.
Huber et al., *Mol. Breed.*, 10:19-30, 2002.
Hudspeth and Grula, *Plant Mol. Biol.*, 12:579-589, 1989.
Huub et al., *Plant Molec. Biol.*, 21:985, 1993.
Ikuta et al., *Bio/technol.*, 8:241-242, 1990.
Ishidia et al., *Nat. Biotechnol.*, 14(6):745-750, 1996.
Janakiraman, et al., *In Vitro Cell. Dev. Biol.-Plant*, 38:404-414, 2002.
Jones et al., *Science*, 266:7891, 1994.
Katz et al., *J. Gen. Microbiol.*, 129:2703-2714, 1983.
Keshwani, D. R., and J. J. Cheng "Switchgrass for bioethanol and other value-added applications: A review" *Bioresource Technology* 100:1515-1523, 2009.
Kirihara et al., *Gene*, 71(2):359-370, 1988.
Klee et al., *BioTechnology*, 3(7):637-642, 1985.
Knutzon et al., *Proc. Natl. Acad. Sci. USA*, 89:2624, 1992.
Lawton et al., *Plant Mol. Biol.* 9:315-324, 1987.
Lee et al., *EMBO J.*, 7:1241, 1988.
Lehner et al., *Brief Funct Genomic Proteomic*, April 3(1):68-83, 2004.
Li and Qu, *Plant Cell Rep.*, 22:403-407, 2004.
Llewellyn et al., *J. Mol. Biol.* 195(1):115-23, 1987.
Logemann et al., *Biotechnology*, 10:305, 1992.
Marshall et al., *Theor. Appl. Genet.*, 83:4:35, 1992.
Martin et al., *Science*, 262: 1432, 1993.
McCormac et al., *Euphytica*, 99(1):17-25, 1998.

McDonough et al., *J. Biol. Chem.*, 267(9):5931-5936, 1992.
McLaughlin, S. B., and L. A. Kszos "Development of switchgrass (*Panicum virgatum*) as a bioenergy feedstock in the United States" *Biomass and Bioenergy* 28:515-535, 2005.
McLaughlin and Walsh, *Biomass and Bioenergy*, 14(4):317-324, 1998.
Miki et al., *Theor. Appl. Genet.*, 80:449, 1990.
Mindrinos et al., *Cell*, 78(6):1089-1099, 1994.
Murakami et al., *Mol. Gen. Genet.*, 205:42-50, 1986.
Murashige and Skoog, *Physiol. Plant.*, 15:473-497, 1962.
Odell et al., *Nature*, 313:810-812, 1985.
Ogawa et al., *Sci. Rep.*, 13:42-48, 1973.
Ow et al., *Science*, 234:856-859, 1986.
PCT Appln. WO 91/13972
PCT Appln. WO 94/000992
PCT Appln. WO 97/4103
PCT Appln. WO 97/41228
Pen et al., *Biotechnology*, 10:292, 1992.
Popelka and Altpeter, *Mol. Breed.*, 11:203-211, 2003.
Potrykus et al., *Mol. Gen. Genet.*, 199(2):169-177, 1985.
Potrykus et al., *Mol. Gen. Genet.*, 199:183-188, 1985.
Prasher et al., *Biochem. Biophys. Res. Commun.*, 126(3):1259-1268, 1985.
Przibila et al., *Plant Cell*, 3:169, 1991.
Raboy et al., *Plant Physiol.*, 124(1):355-368.
Rae et al., *Australian Journal of Plant Physiology*, 28(4):289-297, 2001.
Reddy et al., *Plant Mol. Biol.*, 22(2):293-300, 1993.
Reichel et al., *Proc. Natl. Acad. Sci. USA*, 93(12):5888-5893, 1996.
Rogers et al., *Methods Enzymol.*, 153:253-277, 1987.
Sallaud et al., *Theor. Appl. Genet.*, 106:1396-1408, 2003.
Sambrook et al., In: *Molecular cloning*, Cold Spring Harbor Laboratory Press, Cold Spring Harbor, N.Y., 1989.
Sergaard et al., *J. Biol. Chem.*, 268:22480, 1993.
Sheen et al., *Plant J.*, 8(5):777-784, 1995.
Shiroza et al., *J. BacteoL.*, 170:810, 1988.
Spangenberg et al., In: *Biotechnology in forage and turf grass improvement*, Springer, Berlin, 1998.
Spangenberg et al., *J. Plant Physiol.*, 145:693-701, 1995.
Spencer et al., *Plant Mol. Biol.*, 18(2):201-210, 1992.
Stalker et al., *Science*, 242:419-422, 1988.
Steinmetz et al., *Mol. Gen. Genet.*, 20:220, 1985.
Sticklen, *Current Opinion in Biotechnology*, 17(3):315-319, 2006.
Sullivan et al., *Mol. Gen. Genet.*, 215(3):431-440, 1989.
Sumitani et al., *Bioscience, Biotechnology, and Biochemistry*, 57(8):1243-1248, 1993.
Sutcliffe, *Proc. Natl. Acad. Sci. USA*, 75:3737-3741, 1978.
Tabe et al., *Genetica*, 90:181-200, 1993.
Tavladoraki et al., *Nature*, 366:469, 1993.
Taylor et al., Seventh Int'l Symposium on Molecular Plant-Microbe Interactions, Edinburgh, Scotland, Abstract W97, 1994.
Thillet et al., *J. Biol. Chem.*, 263:12500-12508, 1988.
Thomas et al., *Plant Sci.* 69:189-198, 1990.
Thompson et al., *EMBO J.*, 6(9):2519-2523, 1987.
Tian et al., *Genes Dev.*, 11(1):72-82, 1997.
Tingay et al., *Plant J.*, 11(6):1369-1376, 1997.
Twell et al., *Plant Physiol.*, 91:1270-1274, 1989.
Van Damme et al., *Plant Molec. Biol.*, 24:25, 1994.
Van Hartingsveldt et al., *Gene*, 127:87, 1993.
Vasil et al., *Bio/Technology*, 10:667-674, 1992.
Vasil et al., *Plant Physiol.*, 91:1575-1579, 1989.
Wan and Lemaux, *Plant Physiol.*, 104:37-48, 1994.
Wang and Ge, *J. Plant Physiol.*, 162:103-113, 2005.
Wang, Z-Y. and Ge, Y. "Recent advances in genetic transformation of forage and turf grasses."*In Vitro Cell. Dev. Biol. Plant* 42: 1-8, 2006.
Wang et al., *Crit. Rev. Plant Sci.*, 20:573-619, 2001.
Wang et al., *In Vitro Cell. Dev. Biol. Plant*, 39:277-282, 2003.
Wang et al., *Molec. Cell. Biol.*, 12(8):3399-3406, 1992.
Wang et al., *Plant Cell Rep.*, 22:903-909, 2004.
Whetten and Sederoff, *Forest Ecology and Management*, 43(3):301-316, 1991.
Yang and Russell, *Proc. Natl. Acad. Sci. USA*, 87:4144-4148, 1990.
Zhao et al., *Plant Mol. Biol.*, 44:789-798, 2000.
Zukowsky et al., *Proc. Natl. Acad. Sci. USA*, 80:1101-1105, 1983.

What is claimed is:

1. A method of transforming a grass plant cell comprising contacting a non-stolon or non-rhizome nodal explant, or an inflorescence explant, from a grass plant with an *Agrobacterium* comprising a DNA of interest, wherein the explant is contacted with the *Agrobacterium* without first forming a callus culture of cells from the explant, wherein at least a first cell of the explant is transformed with the DNA of interest; wherein the grass plant is switchgrass and wherein the explant is excised from the plant prior to contacting the explant with the *Agrobacterium*.

2. The method of claim 1, further comprising regenerating a switchgrass plant from the cell.

3. The method of claim 2, wherein regenerating a switchgrass plant comprises culturing the explant after contacting the explant with *Agrobacterium* to induce formation of roots or shoots; allowing roots or shoots to form from the explant; and cultivating the explant under plant growth conditions to produce a transgenic grass plant comprising the DNA of interest.

4. The method of claim 3, further comprising growing said plant to sexual maturity and obtaining a transgenic seed therefrom.

5. The method of claim 1, wherein said DNA of interest comprises a polynucleotide encoding a polypeptide, antisense construct or siRNA construct.

6. The method of claim 5, wherein the polynucleotide is operably linked to a promoter functional in grass plants.

7. The method of claim 6, wherein the promoter is a constitutive promoter, inducible promoter or tissue specific promoter.

8. The method of claim 5, wherein the polynucleotide confers a trait selected from the group consisting of herbicide resistance, insect resistance, disease resistance, pest resistance, improved nutritional quality, modified carbohydrate metabolism, modified lipid metabolism, increased biomass, altered lignin content, increased plant digestibility, increased biomass digestibility, altered lignin biosynthesis and modified fermentable carbohydrate content.

9. The method of claim 5, wherein the polypeptide comprises a selectable marker or a screenable marker.

10. The method of claim 9, wherein the selectable marker confers resistance to a selective agent.

11. The method of claim 10, further comprising contacting the explant with the selective agent and selecting an explant with tolerance to the agent.

12. A method of producing food, feed or biomass comprising (a) obtaining a plant by the method of claim 2; and (b) producing food, feed or biomass from the plant or part thereof.

13. A method of plant breeding comprising (a) obtaining a plant by the method of claim 2; and (b) crossing said plant with a second switchgrass plant.

* * * * *